United States Patent [19]

Ishii

[11] Patent Number: 5,267,951
[45] Date of Patent: Dec. 7, 1993

[54] TAPING SUPPORTER

[76] Inventor: Hikaru Ishii, 1-13-27 Kotesashi, Tokorozawa-city 359, Japan

[21] Appl. No.: 814,703

[22] Filed: Dec. 30, 1991

[30] Foreign Application Priority Data

Jul. 31, 1991 [JP] Japan .................. 3-191892

[51] Int. Cl.⁵ .................. A61F 3/00; A61F 13/00
[52] U.S. Cl. .................. 602/26; 602/14; 602/23; 602/20; 602/63
[58] Field of Search .................. 602/23, 26, 60–65, 602/14, 20

[56] References Cited

U.S. PATENT DOCUMENTS

| | | | |
|---|---|---|---|
| 2,070,810 | 2/1937 | Saling | 602/14 X |
| 3,046,981 | 7/1962 | Biggs, Jr. et al. | 602/26 |
| 3,387,305 | 6/1968 | Shafer | 602/26 X |
| 3,442,265 | 5/1969 | Maluen | 602/14 X |
| 4,366,813 | 1/1983 | Nelson | 602/26 |
| 4,724,831 | 2/1988 | Huntjens | 602/26 |
| 4,765,318 | 8/1988 | Tranberg et al. | 602/26 |
| 5,016,621 | 5/1991 | Bender | 602/26 |
| 5,086,761 | 2/1992 | Ingram | 602/26 |

FOREIGN PATENT DOCUMENTS 60-13464 4/1985 Japan .

*Primary Examiner*—Steven A. Bratlie
*Attorney, Agent, or Firm*—Kanesaka and Takeuchi

[57] ABSTRACT

A taping supporter of the invention is worn around a joint and a surrounding portion of a user for tightly support the same. The taping supporter is formed of a cylindrical body having a size slightly smaller than a size of the joint and the surrounding portion to be worn. The cylindrical body is made of a resilient material to tightly hold and support the joint and the surrounding portion. Signs or wrapping marks are printed on the outer surface of the cylindrical body to apply tapes thereon along the signs. When used, the cylindrical body is worn and the tapes are applied along the signs. Consequently, the joint and the surrounding portion are well supported by the cylindrical body and the tapes.

4 Claims, 1 Drawing Sheet

TAPING SUPPORTER

BACKGROUND OF THE INVENTION AND RELATED ART STATEMENT

The present invention relates to a taping supporter for holding and supporting a part of a body. When tapes are applied on the taping supporter, it functions as a supporter and a taping to prevent damage of a joint and its surrounding area.

In sport or exercise, when a body is moved, a part of a body which is not used frequently is liable to be damaged or impaired. Especially, if a body has a weak portion, such weak portion is further damaged. The damage generally occurs at joints, tendons and muscles. Examples of such damages or troubles are, so called, tennis elbow, jumping knee, jogging knee and so on.

In order to prevent damages or troubles caused by sport or exercise, it is preferable to support a weak portion of a body. For this purpose, a supporter made of an elastic material is known to elastically support or hold a muscle or tendon around a joint.

Also, taping is known to protect a muscle or tendon. The taping means to put or apply tapes along the muscle or tendon so that excessive load is not applied to the muscle or tendon by the tapes. Damages or troubles by excessive load applied to the muscle or tendon are effectively prevented by the taping.

The supporter and the taping have advantages as stated above. However, they have disadvantages as well.

In particular, the supporter can be easily worn at a required portion, but the supporter elastically tightens or holds the entire area of a joint. Namely, since the supporter has elasticity in all directions, it is impossible to support or strengthen the muscle in a specific direction thereto.

For example, in case the supporter is worn around a joint, the supporter can not support or strengthen a muscle against torsion of the joint. In this case, the disadvantage can be improved slightly by using a supporter with strong tension. However, if the tension of the supporter is increased, blood vessels are compressed to reduce blood flow in the blood vessels. Also, movement of the joint is excessively limited.

On the other hand, the taping is effective for supporting a muscle at a desired portion while allowing the joint to move in a necessary range. However, the taping must be made in specific orders and directions. Otherwise, even if the taping is made, muscle or tendon can not be effectively supported. Therefore, doctors or trainers with sufficient knowledge and experiences can only apply the tapes.

Also, if the taping is applied around a joint to be moved frequently, the taping applied around the joint may loose. Therefore, effective taping is not made at the joint moved frequently. Further, the taping is not useful for a sport made for a long time.

In view of the above disadvantages, a taping device was made so that a taping can be made easily by a user, which was published in Japanese Utility Model Publication No. 60-13464 published on Apr. 30, 1985.

The taping device is formed of a resilient material, on which locations and order for applying tapes are imprinted. When used, the user wears the taping device at a predetermined position, and the tapes are applied at the specific locations and order as printed on the taping device. As a result, basic taping can be easily made by a user.

The taping device as explained above is useful for a user. However, since the taping device helps applying the tapes on a required portion, the taping device has disadvantages as in the taping explained before. Namely, it is not effective to a portion moved frequently.

The present invention has been made with reference to the disadvantages as explained above.

Accordingly, an object of the present invention is to provide a taping supporter for providing optimum tension and support to a joint and its surrounding area by combining a supporter and a taping.

Another object of the invention is to provide a taping supporter as stated above, wherein a taping can be easily made by a user.

A further object of the invention is to provide a taping supporter as stated above, which is effective for sweat or moisture.

Further objects and advantages of the invention will be apparent from the following description of the invention.

SUMMARY OF THE INVENTION

In accordance with the present invention, a taping supporter is worn around a joint and a surrounding portion of a user for snugly and tightly supporting the same.

The taping supporter is formed of a cylindrical body having a size slightly smaller than a size of the joint and the surrounding portion to be worn. The cylindrical body is made of a resilient material to tightly hold and support the joint and the surrounding portion.

Accordingly, when the cylindrical body is worn around the joint, the joint and the surrounding portion are tightly covered. The cylindrical body operates as a supporter, but it does not hold the joint and the surrounding portion so strongly.

The cylindrical body has signs printed thereon to apply tapes on the cylindrical body along the signs. When a taping is made, tapes for this purpose are put on the cylindrical body along and in the order of the signs.

In the present invention, the cylindrical body supports the joint and the surrounding portion tightly as a supporter, and after the taping is made, the joint and the surrounding portion are tightly restricted by the tapes. The joint and the surrounding portion are protected by the functions of the supporter and the tapes.

The cylindrical body is made of resilient rubber to tightly hold the joint and the surrounding portion. Preferably, the cylindrical body includes a plurality of small holes or pin holes extending throughout the cylindrical body. The small holes permit sweat or moisture inside the cylindrical body to pass therethrough. Therefore, the cylindrical body does not move by sweat in use. Also, skin is not irritated by sweat.

DETAILED DESCRIPTION OF A PREFERRED EMBODIMENT

Figure 1:
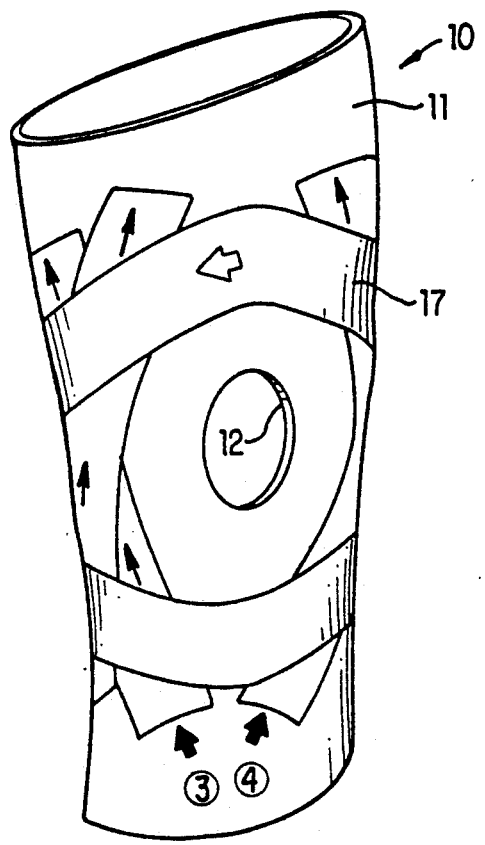
FIG. 1 is a perspective view of a taping supporter of the invention.
Figure 2:
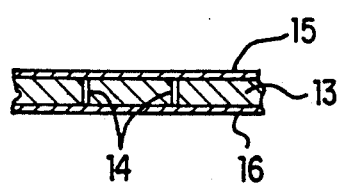
FIG. 2 is a part of a section view of the taping supporter.
Figure 3:
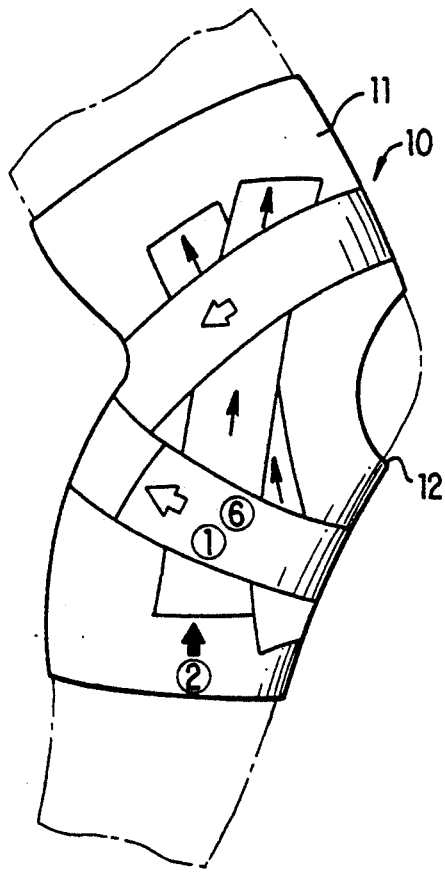
FIG. 3 is a perspective view for showing that the taping supporter is worn on a knee of a user.

A taping supporter 10 of the invention is shown in FIGS. 1-3. The taping supporter 10 is designed for a knee and is formed of a cylindrical body 11 with an opening 12 in the middle portion thereof.

As shown in FIG. 2, the cylindrical body 11 is formed of a center portion 13 with a plurality of small holes 14, an outer layer 15 and an inner layer 16. The center portion 13 is made of flexible and resilient rubber, such as chloroprene rubber, while the outer layer 15 and the inner layer 16 are made of strong cloth, such as nylon. In this example, the thickness of the center portion 13 is 3 mm to provide sufficient resiliency.

The small holes 14 are formed in the center portion 13 so that sweat or moisture inside the cylindrical body 11 can pass therethrough. As a result, the cylindrical body 11 does not slip around the knee by sweat. Also, rash by sweat can be effectively prevented.

The cylindrical body 11 is made slightly smaller than the knee to be worn so that the cylindrical body 11 tightly hold the knee and its surrounding portion. It is important to use the cylindrical body at the proper size.

On the outer surface of the outer layer 15, wrapping marks 17 are printed. The wrapping marks generally include rectangular portions with numbers. Tapes which are known and available in a market, are attached over the rectangular portions on the outer layer 15 in accordance with the numeral or order printed thereon.

The wrapping marks 17 are different in the joints or parts of the body and are determined based on the direction of the muscles and experiences. Since the direction of the muscles is common for each joint, the user may apply the tapes in accordance with the instructions printed thereon without experiences.

The size and shape of the cylindrical body 10 and the marks 17 printed thereon are different based on the joints or parts that the taping supporter is applied. In the present invention, the tapes may be applied in accordance with the instructions printed on the cylindrical body.

In case the taping supporter 10 of the invention is used, a user wears the cylindrical body 11 on the knee such that the opening 12 is located above the top of the knee, as shown in FIG. 3. As a result, movement of the knee is not excessively prevented by the cylindrical body 11. The knee and the surrounding portion are tightly supported by the cylindrical body 11. Thereafter, the tapes are applied over the cylindrical body 11 as indicated thereon.

In the examples shown in the drawings, the tape is at first applied tightly from numeral 1 around the knee in the form of numeral 8, and the tap is cut. Then, two pieces of the tapes are applied at one side of the knee to intersect with each other as shown in numerals 2 and 3. The tapes are also applied at the opposite side of the knee, which is marked as numerals 4 and 5 (5 is not seen). Finally, the tape is applied around the knee in the form of numeral 8 as in the first taping, which is indicated as numeral 6.

In the above example, two sets of the crossing tapes are situated on both sides of the knee, and other tapes are placed above and below the knee. This taping is simple, but trouble of the knee is effectively prevented by this simple taping. Especially, the above taping restricts excessive lateral movement or twist of the knee, so that muscle around the knee is effectively protected.

When the taping is finished, movement of the knee is restricted and the muscles are also supported or protected by the tapes applied on the cylindrical body.

In the present invention, the taping is made above the supporter. The supporter protects a joint from shocks applied thereto, and holds the joint tightly at the proper position. The taping protects or prevents excessive movement of the muscle.

In case the supporter and the taping are combined, looseness of the tapes is effectively prevented because of resiliency of the supporter. Therefore, the tapes are effective for a long period of time.

In the present invention, wrapping marks are printed on the supporter. Therefore, after the supporter is worn, the taping can be easily made above the supporter. In the present invention, advantages of the supporter and the taping are effectively utilized. A joint and its surrounding portion are properly supported and protected.

Needless to say, in one particular joint, the taping supporters with several different sizes are prepared, and the user selects the proper size to snugly and tightly support the joint to be worn.

In the drawings, the taping supporter for knee is shown. However, the taping supporter for ankle, elbow and so on can be made in accordance with the present invention. Signs on the taping supporter are different for the different taping supporters. Also, in one particular taping supporter, signs may be changed for specific purpose, such as protecting particular muscle.

While the invention has been explained with reference to the specific embodiment of the invention, the explanation is illustrative and the invention is limited only by the appended claims.

What is claimed is:

1. A taping supporter adapted to be worn around a joint and its surrounding portion of a user for snugly and tightly supporting the same, comprising, a cylindrical body having a size slightly smaller than a size of the joint and the surrounding portion to be worn, said cylindrical body being made of resilient rubber and resilient linings fixed on both entire surfaces of the resilient rubber, said cylindrical body tightly holding and supporting the joint and the surrounding portion so that the cylindrical body operates as a supporter for the joint and the surrounding portion when worn by the user, said resilient rubber having a plurality of small holes penetrating therethrough and formed over an entire area of the cylindrical body and the resilient linings covering the entire surfaces of the resilient rubber without having any holes therein to provide smooth surfaces over the cylindrical body so that moisture and liquid inside the cylindrical body pass through the resilient rubber and the resilient linings, and signs printed on an outer surface of the resilient lining of the cylindrical body, said signs being formed of elongated lines for indicating application portions of tapes and numerals for indicating orders of applying the tapes so that when the cylindrical body is worn around the joint and the surrounding portion, and the tapes are applied on and around the cylindrical body along the signs with predetermined orders, the joint and the surrounding portion are well supported by the cylindrical body as a supporter and the tapes fixed on the cylindrical body.

2. A taping supporter according to claim 1, wherein said small holes are pin holes.

3. A taping supporter according to claim 2, wherein said resilient rubber is a chloroprene rubber having a thickness about 3 mm.

4. A combination of tapes and a taping supporter adapted to be worn around a joint and its surrounding portion of a user for snugly and tightly supporting the same, comprising, a taping supporter including a cylindrical body having a size slightly smaller than a size of the joint and the surrounding portion to be worn, said cylindrical body being made of resilient rubber and resilient linings fixed on both entire surfaces of the resilient rubber, said cylindrical body tightly holding and supporting the joint and the surrounding portion so that the cylindrical body operates as a supporter for the joint and the surrounding portion when worn by the user, said resilient rubber having a plurality of small holes penetrating therethrough and formed over an entire area of the cylindrical body and the resilient linings covering the entire surfaces of the resilient rubber without having any holes therein to provide smooth surfaces over the cylindrical body so that moisture and liquid inside the cylindrical body pass through the resilient rubber and the resilient linings; and signs printed on an outer surface of the resilient lining of the cylindrical body, said signs being formed of elongated lines and numerals, and tapes applied onto the elongated lines in the order of the numerals printed on the cylindrical body so that when the cylindrical body is worn around the joint and the surrounding portion, and the tapes are applied on and around the cylindrical body along the signs and according to the predetermined orders, the joint and the surrounding portion are well supported by the cylindrical body as a supporter and the tapes fixed on the cylindrical body.

* * * * *